(12) United States Patent
Thommen et al.

(10) Patent No.: US 10,863,994 B2
(45) Date of Patent: *Dec. 15, 2020

(54) FLEXIBLE TRANSPORT AUGER

(71) Applicant: Medos International Sàrl, Le Locle (CH)

(72) Inventors: Daniel Thommen, Liestal (CH); Joern Richter, Kandern (DE); Salman Chegini, Bern (CH); Joseph Peterson, South Dartmouth, MA (US); Michael J. O'Neil, West Barnstable, MA (US); Gabriel Emmett Greeley, Andover, MA (US); Matthew Brian De Nardo, Watertown, MA (US); Serge Cyril Roux, Boston, MA (US); Ashley Lauren Whitney, Somerville, MA (US); John DiVincenzo, Braintree, MA (US); Thomas Martin, Riverside, RI (US)

(73) Assignee: Medos International Sàrl, Le Locle (CH)

( * ) Notice: Subject to any disclaimer, the term of this patent is extended or adjusted under 35 U.S.C. 154(b) by 218 days.

This patent is subject to a terminal disclaimer.

(21) Appl. No.: 15/968,437

(22) Filed: May 1, 2018

(65) Prior Publication Data

US 2018/0242984 A1    Aug. 30, 2018

Related U.S. Application Data

(63) Continuation of application No. 14/571,874, filed on Dec. 16, 2014, now Pat. No. 9,980,737.

(Continued)

(51) Int. Cl.
*A61B 17/32* (2006.01)
*A61B 17/16* (2006.01)
(Continued)

(52) U.S. Cl.
CPC .......... *A61B 17/1671* (2013.01); *A61B 17/30* (2013.01); *A61B 17/32002* (2013.01);
(Continued)

(58) Field of Classification Search
CPC ................................ A61B 17/16–1642; A61B 17/32–2017/320791
See application file for complete search history.

(56) References Cited

U.S. PATENT DOCUMENTS

| 4,573,448 A | 3/1986 | Kambin |
| 4,646,738 A | 3/1987 | Trott |

(Continued)

FOREIGN PATENT DOCUMENTS

| CN | 102727309 B | 11/2014 |
| DE | 94 15 039 U1 | 11/1994 |

(Continued)

OTHER PUBLICATIONS

**International Search Report and Written Opinion for Application No. PCT/US15/43554, dated Nov. 19, 2015 (8 pages).

(Continued)

*Primary Examiner* — Zade Coley
(74) *Attorney, Agent, or Firm* — Nutter McClennen & Fish LLP (57) ABSTRACT

A flexible auger design for low-torque transmitting drive shafts, which allows effective tissue material transport through curved, flexible tubes and channels. A hollow auger has a hollow center, so that the helical member hugs the inner wall of the tube and material is transported along the center axis and the inner wall of the tube. The hollow flexible auger allows for transportation of material from an operative location in the patient (material removal) as well as to operative location in the patient (material delivery).

11 Claims, 9 Drawing Sheets

Related U.S. Application Data (60) Provisional application No. 62/032,754, filed on Aug. 4, 2014.

(51) Int. Cl.
*A61B 17/30* (2006.01)
*A61B 17/00* (2006.01)

(52) U.S. Cl.
CPC ........... *A61B 2017/00261* (2013.01); *A61B 2017/00685* (2013.01); *A61B 2017/320024* (2013.01)

(56) References Cited

U.S. PATENT DOCUMENTS

| | | | |
|---|---|---|---|
| 4,653,496 A * | 3/1987 | Bundy | A61B 17/3207 600/564 |
| 4,678,459 A | 7/1987 | Onik et al. | |
| 4,732,154 A * | 3/1988 | Shiber | A61B 17/22012 606/108 |
| 4,863,430 A | 9/1989 | Klyce et al. | |
| 4,888,146 A | 12/1989 | Dandeneau | |
| 4,914,060 A * | 4/1990 | Seas | H01R 13/625 439/314 |
| 5,041,082 A * | 8/1991 | Shiber | A61B 17/22012 604/22 |
| 5,078,723 A * | 1/1992 | Dance | A61B 17/3207 604/22 |
| 5,080,662 A | 1/1992 | Paul | |
| 5,135,531 A * | 8/1992 | Shiber | A61B 8/12 606/159 |
| 5,195,541 A | 3/1993 | Obenchain | |
| 5,285,795 A | 2/1994 | Ryan et al. | |
| 5,395,317 A | 3/1995 | Kambin | |
| 5,439,464 A | 8/1995 | Shapiro | |
| 5,529,580 A | 6/1996 | Kusunoki et al. | |
| 5,540,706 A | 7/1996 | Aust et al. | |
| 5,569,290 A | 10/1996 | McAfee | |
| 5,591,187 A * | 1/1997 | Dekel | A61B 17/32002 606/170 |
| 5,601,569 A | 2/1997 | Pisharodi | |
| 5,662,300 A | 9/1997 | Michelson | |
| 5,688,222 A | 11/1997 | Hluchy et al. | |
| 5,730,754 A | 3/1998 | Obenchain | |
| 5,733,242 A | 3/1998 | Rayburn et al. | |
| 5,735,792 A | 4/1998 | Vanden Hoek et al. | |
| 5,820,623 A | 10/1998 | Ng | |
| 5,885,300 A | 3/1999 | Tokuhashi et al. | |
| 5,894,369 A | 4/1999 | Akiba et al. | |
| 5,899,425 A | 5/1999 | Corey, Jr. et al. | |
| 5,954,635 A | 9/1999 | Foley et al. | |
| 6,033,105 A | 3/2000 | Barker et al. | |
| 6,053,907 A | 4/2000 | Zirps | |
| 6,063,021 A | 5/2000 | Hossain et al. | |
| 6,110,182 A | 8/2000 | Mowlai-Ashtiani | |
| 6,139,508 A * | 10/2000 | Simpson | A61B 10/06 600/564 |
| 6,200,322 B1 | 3/2001 | Branch et al. | |
| 6,234,961 B1 | 5/2001 | Gray | |
| 6,283,966 B1 | 9/2001 | Houfburg | |
| 6,286,179 B1 | 9/2001 | Byrne | |
| 6,296,644 B1 | 10/2001 | Saurat et al. | |
| 6,322,498 B1 | 11/2001 | Gravenstein et al. | |
| 6,354,992 B1 | 3/2002 | Kato | |
| 6,371,968 B1 | 4/2002 | Kogasaka et al. | |
| 6,383,191 B1 | 5/2002 | Zdeblick et al. | |
| 6,447,446 B1 | 9/2002 | Smith et al. | |
| 6,468,289 B1 | 10/2002 | Bonutti | |
| 6,558,407 B1 | 5/2003 | Ivanko et al. | |
| 6,575,899 B1 | 6/2003 | Foley et al. | |
| 6,579,281 B2 | 6/2003 | Palmer et al. | |
| 6,626,830 B1 | 9/2003 | Califiore et al. | |
| 6,648,915 B2 | 11/2003 | Sazy | |
| 6,676,597 B2 | 1/2004 | Guenst et al. | |
| 6,688,564 B2 | 2/2004 | Salvermoser et al. | |
| 6,758,809 B2 | 7/2004 | Briscoe et al. | |
| 6,808,505 B2 | 10/2004 | Kadan | |
| 6,887,198 B2 | 5/2005 | Phillips et al. | |
| 6,983,930 B1 | 1/2006 | La Mendola et al. | |
| 7,087,058 B2 | 8/2006 | Cragg | |
| 7,104,986 B2 | 9/2006 | Hovda et al. | |
| 7,137,949 B2 | 11/2006 | Soirica et al. | |
| 7,182,731 B2 | 2/2007 | Nguyen et al. | |
| 7,341,556 B2 | 3/2008 | Shalman | |
| 7,434,325 B2 | 10/2008 | Foley et al. | |
| 7,591,790 B2 | 9/2009 | Pflueger | |
| 7,594,888 B2 | 9/2009 | Raymond et al. | |
| 7,618,431 B2 | 11/2009 | Roehm, III et al. | |
| 7,636,596 B2 | 12/2009 | Solar | |
| 7,637,905 B2 | 12/2009 | Saadat et al. | |
| 7,641,659 B2 | 1/2010 | Emstad et al. | |
| 7,771,384 B2 | 8/2010 | Ravo | |
| 7,794,456 B2 | 9/2010 | Sharps et al. | |
| 7,803,159 B2 * | 9/2010 | Perez-Cruet | A61B 17/1671 606/79 |
| 7,811,303 B2 | 10/2010 | Fallin et al. | |
| 7,931,579 B2 | 4/2011 | Bertolero et al. | |
| 7,946,981 B1 | 5/2011 | Cubb | |
| 7,951,141 B2 | 5/2011 | Sharps et al. | |
| 7,959,564 B2 | 6/2011 | Ritland | |
| 7,988,623 B2 | 8/2011 | Pagliuca et al. | |
| 8,007,492 B2 | 8/2011 | DiPoto et al. | |
| 8,038,606 B2 | 10/2011 | Otawara | |
| 8,043,381 B2 | 10/2011 | Hestad et al. | |
| 8,062,218 B2 | 11/2011 | Sebastian et al. | |
| 8,092,464 B2 | 1/2012 | McKay | |
| 8,096,944 B2 | 1/2012 | Harrel | |
| 8,096,957 B2 * | 1/2012 | Conquergood | A61B 17/320016 600/562 |
| 8,201,563 B2 * | 6/2012 | Conquergood | A61B 17/320016 128/898 |
| 8,202,216 B2 | 6/2012 | Melkent et al. | |
| 8,236,006 B2 | 8/2012 | Hamada | |
| 8,333,690 B2 | 12/2012 | Ikeda | |
| 8,360,970 B2 | 1/2013 | Mangiardi | |
| 8,372,131 B2 | 2/2013 | Hestad et al. | |
| 8,382,048 B2 | 2/2013 | Nesper et al. | |
| 8,397,335 B2 | 3/2013 | Gordin et al. | |
| 8,435,174 B2 | 5/2013 | Cropper et al. | |
| 8,460,180 B1 | 6/2013 | Zarate et al. | |
| 8,460,186 B2 | 6/2013 | Ortiz et al. | |
| 8,460,310 B2 | 6/2013 | Stern | |
| 8,518,087 B2 | 8/2013 | Lopez et al. | |
| 8,535,220 B2 | 9/2013 | Mondschein | |
| 8,556,809 B2 | 10/2013 | Vijayanagar | |
| 8,585,726 B2 | 11/2013 | Yoon et al. | |
| 8,602,979 B2 | 12/2013 | Kitano | |
| 8,622,894 B2 | 1/2014 | Banik et al. | |
| 8,636,655 B1 | 1/2014 | Childs | |
| 8,690,764 B2 | 4/2014 | Clark et al. | |
| 8,721,536 B2 | 5/2014 | Marino et al. | |
| 8,740,779 B2 | 6/2014 | Yoshida | |
| 8,784,421 B2 | 7/2014 | Carrison et al. | |
| 8,821,378 B2 | 9/2014 | Morgenstern Lopez et al. | |
| 8,834,507 B2 | 9/2014 | Mire et al. | |
| 8,845,734 B2 | 9/2014 | Weiman | |
| 8,852,242 B2 | 10/2014 | Morgenstern Lopez et al. | |
| 8,870,753 B2 | 10/2014 | Boulais et al. | |
| 8,870,756 B2 | 10/2014 | Maurice | |
| 8,876,712 B2 | 11/2014 | Yee et al. | |
| 8,894,573 B2 | 11/2014 | Loftus et al. | |
| 8,894,653 B2 | 11/2014 | Solsberg et al. | |
| 8,926,502 B2 | 1/2015 | Levy et al. | |
| 8,932,207 B2 | 1/2015 | Greenburg et al. | |
| 8,932,360 B2 | 1/2015 | Womble et al. | |
| 8,936,605 B2 | 1/2015 | Greenberg | |
| 8,974,381 B1 | 3/2015 | Lovell et al. | |
| 8,986,199 B2 | 3/2015 | Weisenburgh, II et al. | |
| 8,992,580 B2 | 3/2015 | Bar et al. | |
| 9,028,522 B1 | 5/2015 | Prado | |
| 9,050,146 B2 | 6/2015 | Woolley et al. | |

(56) References Cited

U.S. PATENT DOCUMENTS

| | | |
|---|---|---|
| 9,055,936 B2 | 6/2015 | Mire et al. |
| 9,072,431 B2 | 7/2015 | Adams et al. |
| 9,078,562 B2 | 7/2015 | Poll et al. |
| 9,131,948 B2 | 9/2015 | Fang et al. |
| 9,144,374 B2 | 9/2015 | Maurice, Jr. |
| 9,198,674 B2 | 12/2015 | Benson et al. |
| 9,211,059 B2 | 12/2015 | Drach et al. |
| 9,216,016 B2 | 12/2015 | Fiechter et al. |
| 9,216,125 B2 | 12/2015 | Sklar |
| 9,232,935 B2 | 1/2016 | Brand et al. |
| 9,247,997 B2 | 2/2016 | Stefanchik et al. |
| 9,265,491 B2 | 2/2016 | Lins et al. |
| 9,277,928 B2 | 3/2016 | Morgenstern Lopez |
| 9,307,972 B2 | 4/2016 | Lovell et al. |
| 9,320,419 B2 | 4/2016 | Kirma et al. |
| RE46,007 E | 5/2016 | Banik et al. |
| RE46,062 E | 7/2016 | James et al. |
| 9,386,971 B1 | 7/2016 | Casey et al. |
| 9,387,313 B2 | 7/2016 | Culbert et al. |
| 9,414,828 B2 | 8/2016 | Abidin et al. |
| 9,486,296 B2 | 11/2016 | Mire et al. |
| 9,492,194 B2 | 11/2016 | Morgenstern Lopez et al. |
| 9,510,853 B2 | 12/2016 | Aljuri et al. |
| 9,526,401 B2 | 12/2016 | Saadat et al. |
| 9,579,012 B2 | 2/2017 | Vazales et al. |
| 9,603,510 B2 | 3/2017 | Ammirati |
| 9,603,610 B2 | 3/2017 | Richter et al. |
| 9,610,007 B2 | 4/2017 | Kienzle et al. |
| 9,610,095 B2 | 4/2017 | To |
| 9,629,521 B2 | 4/2017 | Ratnakar |
| 9,655,605 B2 | 5/2017 | Serowski et al. |
| 9,655,639 B2 | 5/2017 | Mark |
| 9,668,643 B2 | 6/2017 | Kennedy, II et al. |
| 9,675,235 B2 | 6/2017 | Lieponis |
| 9,700,378 B2 | 7/2017 | Mowlai-Ashtiani |
| 9,706,905 B2 | 7/2017 | Levy |
| 9,980,737 B2 | 5/2018 | Thommen et al. |
| 2002/0022762 A1 | 2/2002 | Beane et al. |
| 2002/0138020 A1 | 9/2002 | Pflueger |
| 2003/0083555 A1 | 5/2003 | Hunt et al. |
| 2003/0171744 A1 | 9/2003 | Leung et al. |
| 2003/0191474 A1 | 10/2003 | Cragg et al. |
| 2004/0122446 A1 | 6/2004 | Solar |
| 2004/0127992 A1 | 7/2004 | Serhan et al. |
| 2004/0143165 A1 | 7/2004 | Alleyne |
| 2005/0085692 A1 | 4/2005 | Kiehn et al. |
| 2005/0090848 A1 | 4/2005 | Adams |
| 2005/0187570 A1 | 8/2005 | Nguyen et al. |
| 2005/0256525 A1 | 11/2005 | Culbert et al. |
| 2006/0206118 A1 | 9/2006 | Kim et al. |
| 2007/0055259 A1 | 3/2007 | Norton et al. |
| 2007/0129634 A1 | 6/2007 | Hickey et al. |
| 2007/0149975 A1 | 6/2007 | Oliver et al. |
| 2007/0203396 A1 | 8/2007 | McCutcheon et al. |
| 2007/0225556 A1 | 9/2007 | Ortiz et al. |
| 2007/0260113 A1 | 11/2007 | Otawara |
| 2008/0015621 A1 | 1/2008 | Emanuel |
| 2008/0033251 A1 | 2/2008 | Araghi |
| 2008/0081951 A1 | 4/2008 | Frasier et al. |
| 2008/0109015 A1* | 5/2008 | Chu .............. A61B 17/0469 606/139 |
| 2008/0125856 A1* | 5/2008 | Perez-Cruet ...... A61B 17/1671 623/1.23 |
| 2008/0188714 A1 | 8/2008 | McCaffrey |
| 2009/0018566 A1* | 1/2009 | Escudero ......... A61B 17/32075 606/159 |
| 2009/0024158 A1 | 1/2009 | Viker |
| 2009/0062871 A1 | 3/2009 | Chin et al. |
| 2009/0105543 A1 | 4/2009 | Miller et al. |
| 2009/0156898 A1 | 6/2009 | Ichimura |
| 2009/0187080 A1 | 7/2009 | Seex |
| 2009/0192494 A1* | 7/2009 | Michishita ........ A61M 25/0041 604/525 |
| 2009/0240111 A1 | 9/2009 | Kessler et al. |
| 2009/0287061 A1 | 11/2009 | Feigenbaum et al. |
| 2009/0318765 A1 | 12/2009 | Torii |
| 2010/0004651 A1 | 1/2010 | Biyani |
| 2010/0022841 A1 | 1/2010 | Takahashi et al. |
| 2010/0076476 A1* | 3/2010 | To .................. A61B 17/1617 606/170 |
| 2010/0114147 A1 | 5/2010 | Biyani |
| 2010/0151161 A1 | 6/2010 | Da Rolo |
| 2010/0161060 A1 | 6/2010 | Schaller et al. |
| 2010/0256446 A1 | 10/2010 | Raju |
| 2010/0280325 A1 | 11/2010 | Ibrahim et al. |
| 2010/0284580 A1 | 11/2010 | OuYang et al. |
| 2010/0286477 A1 | 11/2010 | OuYang et al. |
| 2010/0312053 A1 | 12/2010 | Larsen |
| 2011/0028791 A1 | 2/2011 | Marino et al. |
| 2011/0054507 A1 | 3/2011 | Batten et al. |
| 2011/0106261 A1 | 5/2011 | Chin et al. |
| 2011/0125158 A1 | 5/2011 | Diwan et al. |
| 2011/0130634 A1 | 6/2011 | Solitario, Jr. et al. |
| 2011/0295070 A1 | 12/2011 | Yasunaga |
| 2011/0319941 A1 | 12/2011 | Bar et al. |
| 2012/0095296 A1 | 4/2012 | Trieu et al. |
| 2012/0101338 A1 | 4/2012 | O'Prey et al. |
| 2012/0209273 A1 | 8/2012 | Laretzka et al. |
| 2012/0221007 A1 | 8/2012 | Batten et al. |
| 2012/0232350 A1 | 9/2012 | Seex |
| 2012/0232552 A1 | 9/2012 | Morgenstern Lopez et al. |
| 2012/0298820 A1 | 11/2012 | Manolidis |
| 2012/0316400 A1 | 12/2012 | Vijayanagar |
| 2013/0103067 A1* | 4/2013 | Fabro .............. A61B 17/3207 606/170 |
| 2013/0103103 A1 | 4/2013 | Mire et al. |
| 2013/0150670 A1 | 6/2013 | O'Prey et al. |
| 2013/0150674 A1 | 6/2013 | Haig et al. |
| 2013/0172676 A1 | 7/2013 | Levy et al. |
| 2013/0282022 A1 | 10/2013 | Yousef |
| 2013/0289399 A1 | 10/2013 | Choi et al. |
| 2013/0303846 A1 | 11/2013 | Cybulski et al. |
| 2014/0066940 A1 | 3/2014 | Fang et al. |
| 2014/0074170 A1 | 3/2014 | Mertens et al. |
| 2014/0142584 A1 | 5/2014 | Sweeney |
| 2014/0148647 A1 | 5/2014 | Okazaki |
| 2014/0180321 A1* | 6/2014 | Dias .............. A61B 17/32002 606/180 |
| 2014/0194697 A1 | 7/2014 | Seex |
| 2014/0215736 A1 | 8/2014 | Gomez et al. |
| 2014/0257489 A1 | 9/2014 | Warren et al. |
| 2014/0275799 A1 | 9/2014 | Schuele |
| 2014/0276840 A1 | 9/2014 | Richter et al. |
| 2014/0277204 A1 | 9/2014 | Sandhu |
| 2014/0318582 A1 | 10/2014 | Mowlai-Ashtiani |
| 2014/0357945 A1 | 12/2014 | Duckworth |
| 2015/0018623 A1 | 1/2015 | Friedrich et al. |
| 2015/0065795 A1 | 3/2015 | Titus |
| 2015/0073218 A1 | 3/2015 | Ito |
| 2015/0112398 A1 | 4/2015 | Morgenstern Lopez et al. |
| 2015/0164496 A1 | 6/2015 | Karpowicz et al. |
| 2015/0216593 A1 | 8/2015 | Biyani |
| 2015/0223676 A1 | 8/2015 | Bayer et al. |
| 2015/0230697 A1 | 8/2015 | Phee et al. |
| 2015/0342621 A1 | 12/2015 | Jackson, III |
| 2015/0374213 A1 | 12/2015 | Maurice, Jr. |
| 2016/0015467 A1 | 1/2016 | Vayser et al. |
| 2016/0030061 A1 | 2/2016 | Thommen et al. |
| 2016/0066965 A1 | 3/2016 | Chegini et al. |
| 2016/0067003 A1 | 3/2016 | Chegini et al. |
| 2016/0074029 A1 | 3/2016 | 'Connell et al. |
| 2016/0095505 A1 | 4/2016 | Johnson et al. |
| 2016/0106408 A1 | 4/2016 | Ponmudi et al. |
| 2016/0166135 A1 | 6/2016 | Fiset |
| 2016/0174814 A1 | 6/2016 | Igov |
| 2016/0213500 A1 | 7/2016 | Beger et al. |
| 2016/0228280 A1 | 8/2016 | Schuele et al. |
| 2016/0235284 A1 | 8/2016 | Yoshida et al. |
| 2016/0287264 A1 | 10/2016 | Chegini et al. |
| 2016/0296220 A1 | 10/2016 | Mast et al. |
| 2016/0353978 A1 | 12/2016 | Miller et al. |
| 2017/0003493 A1 | 1/2017 | Zhao |
| 2017/0007226 A1 | 1/2017 | Fehling |
| 2017/0027606 A1 | 2/2017 | Cappelleri et al. |

(56) References Cited

U.S. PATENT DOCUMENTS

| | | |
|---|---|---|
| 2017/0042408 A1 | 2/2017 | Washburn et al. |
| 2017/0042411 A1 | 2/2017 | Kang et al. |
| 2017/0065269 A1 | 3/2017 | Thommen et al. |
| 2017/0065287 A1 | 3/2017 | Silva et al. |
| 2017/0086939 A1 | 3/2017 | Vayser et al. |
| 2017/0135699 A1 | 5/2017 | Wolf |
| 2017/0156755 A1 | 6/2017 | Poll et al. |
| 2017/0156814 A1 | 6/2017 | Thommen et al. |
| 2017/0196549 A1 | 7/2017 | Piskun et al. |
| 2017/0224391 A1 | 8/2017 | Biester et al. |

FOREIGN PATENT DOCUMENTS

| | | | |
|---|---|---|---|
| DE | 299 16 026 U1 | 11/1999 | |
| EP | 0 537 116 A1 | 4/1993 | |
| EP | 0 807 415 A2 | 11/1997 | |
| GB | 2481727 A | 1/2012 | |
| JP | 03-80872 A | 4/1991 | |
| JP | 2007-530098 A | 11/2007 | |
| JP | 2011-517601 A | 6/2011 | |
| WO | 96/29014 A1 | 9/1996 | |
| WO | 01/56490 A1 | 8/2001 | |
| WO | 01/089371 A1 | 11/2001 | |
| WO | 02/02016 A1 | 1/2002 | |
| WO | 2004/103430 A3 | 8/2005 | |
| WO | 2008/121162 A1 | 10/2008 | |
| WO | 2009/033207 A1 | 3/2009 | |
| WO | 2013/033426 A2 | 3/2013 | |
| WO | 2013/059640 A1 | 4/2013 | |
| WO | 2014/050236 A1 | 4/2014 | |
| WO | 2014/100761 A2 | 6/2014 | |
| WO | 2014/185334 A1 | 11/2014 | |
| WO | 2016/111373 A1 | 7/2016 | |
| WO | 2016/131077 A1 | 8/2016 | |
| WO | 2016/168673 A1 | 10/2016 | |
| WO | 2017/006684 A1 | 1/2017 | |
| WO | 2017/015480 A1 | 1/2017 | |
| WO | 2017/083648 A1 | 5/2017 | |

OTHER PUBLICATIONS

\*\*Iprenburg, M, "Percutaneous Transforaminal Endoscopic Discectomy: The Thessys Method," in Lewandrowski, K., et al, Minimally Invasive Spinal Fusion Techniques, Summit Communications, 2008 pp. 65-81.
\*\*International Search Report and Written Opinion for Application No. PCT/US2015/048485, dated Feb. 9, 2016. (16 pages).
\*\*International Search Report and Written Opinion for Application No. PCT/US2015/060978, dated Feb. 15, 2016 (8 pages).
\*\*Invitation to Pay Additional Fees for Application No. PCT/US2016/050022, dated Nov. 3, 2016 (2 pages).
\*\*International Search Report and Written Opinion for Application No. PCT/US2016/050022, dated Feb. 1, 2017 (19 pages).
\*\*Jung, K., et al., "A hands-free region-of-interest selection interface for solo surgery with a wide-angle endoscope: preclinical proof of concept," Surg Endosc, 2017, v. 31, pp. 974-980.
Japanese Office Action for Application No. 2017-506356 dated May 7, 2019 (13 pages).

\* cited by examiner

FLEXIBLE TRANSPORT AUGER

CONTINUING DATA

This application is a continuation of U.S. patent application Ser. No. 14/571,874, filed on Dec. 16, 2014, and entitled "Flexible Transport Auger." U.S. patent application Ser. No. 14/571,874 claims the benefit of U.S. Provisional Patent Application No. 62/032,754, filed Aug. 4, 2014, entitled "Flexible Transport Auger." Each of these applications is hereby incorporated by reference in its entirety.

BACKGROUND OF THE INVENTION

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus within its cushioning qualities. These nucleus pulposus cells may also secrete small amounts of cytokines such as interleukin-1β and TNF-α as well as matrix metalloproteinases ("MMPs"). These cytokines and MMPs help regulate the metabolism of the nucleus pulposus cells.

In some instances of disc degeneration disease (DDD), gradual degeneration of the intervetebral disc is caused by mechanical instabilities in other portions of the spine. In these instances, increased loads and pressures on the nucleus pulposus cause the cells within the disc (or invading macrophages) to emit larger than normal amounts of the above-mentioned cytokines. In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins that may cause nerve irritation and pain.

As DDD progresses, toxic levels of the cytokines and MMPs present in the nucleus pulposus begin to degrade the extracellular matrix, in particular, the MMPs (as mediated by the cytokines) begin cleaving the water-retaining portions of the proteoglycans, thereby reducing its water-retaining capabilities. This degradation leads to a less flexible nucleus pulposus, and so changes the loading pattern within the disc, thereby possibly causing delamination of the annulus fibrosus. These changes cause more mechanical instability, thereby causing the cells to emit even more cytokines, thereby upregulating MMPs. As this destructive cascade continues and DDD further progresses, the disc begins to bulge ("a herniated disc"), and then ultimately ruptures, causing the nucleus pulposus to contact the spinal cord and produce pain.

Two of the more common treatments of the herniated disc are the discectomy, total disc replacement and the fusion. In a discectomy, the surgeon removes the bulging disc material. In a fusion, the surgeon clears out a portion of the disc, inserts an intervertebral implant into the disc space. In each case, removal of disc material is an important step.

Automatic transportation of cut disc material has shown to be a significant challenge for automated disc removal tools, especially with small diameter tools designed for minimally invasive surgery. Auger designs have been shown to be very effective in terms of transportation. However, as flexibility and steerability are desirable in disc removal tools, transport augers should also be flexible.

U.S. Pat. No. 7,591,790 ("Pflueger") discloses an apparatus for removing tissue and/or other material from a patient. The apparatus generally includes a handpiece and a tissue removal mechanism connected thereto. The tissue removal mechanism includes a cannula having an open distal tip and an outer diameter of less than about 5 mm, or less than about 2 mm. The mechanism further includes a rotatable element having a distal portion with helical threading. The distal portion of the rotatable element extends beyond the open distal tip of the cannula in order to allow tissue to prolapse between turns of the helical threading. The apparatus is designed to draw soft tissue into the cannula upon rotation of the rotatable element and without the need for supplemental sources of aspiration. The auger of the '790 patent design has a center axis that is solid, which means that the removed material is transported against the auger itself.

US 2013-0103067 ("Fabro") discloses tissue removal devices, wherein the tissue removal device may comprise a handheld housing, a motor, and a tissue removal mechanism coupled to the handheld housing. The tissue removal mechanism may comprise a tubular member, a rotatable elongated member disposed within a lumen of the tubular member, a first impeller distal to the rotatable elongated member, and a second impeller adjacent the first impeller. Fabro discloses a discectomy device comprising a wire wrapped around a core.

U.S. Pat. No. 6,033,105 ("Barker") discloses an integrated bone cement mixing and delivery system using an auger mechanism as the means for advancing the bone cement through the delivery chamber.

SUMMARY OF THE INVENTION

The present invention relates to a flexible hollow auger for low-torque transmitting drive shafts, which allows for effective tissue material transport through curved, flexible tubes and channels.

In one embodiment, the present invention describes a hollow flexible auger. An hollow auger has a hollow center, so that the helical member hugs the inner wall of an outer tube. In use, material is transported along both the center axis and the inner wall of the tube. The hollow flexible auger allows for transportation of material from an operative location in the patient (material removal) as well as to an operative location in the patient (material delivery).

When the hollow flexible auger allows for transportation of tissue material from an operative location in the patient (tissue removal), the target tissue may be soft tissue (such as intervertebral disc tissue) or hard tissue (such as the cancellous bone of a vertebral body).

This design has the potential of providing very low manufacturing costs, which could present an economic advantage in single-use applications. The present invention is especially designed for use in transporting excised material from an intervertebral disc, but could find application in other medical areas in which transportation of solid or liquid material along a curved or flexible tube or channel is desired.

In one embodiment, the flexible auger is made from a standard helical spring and a shrunken heat-shrink tube disposed over and contacting the spring. When the heat-shrink tube is shrunk through application of heat, the final assembly takes on a thread-like appearance.

Therefore, in accordance with the present invention, there is provided a biomedical material transfer device comprising:
a) a transfer element having a proximal end portion, a distal end portion, and an intermediate portion comprising a flexible, hollow auger, and
b) a drive element adapted to rotate the transfer element, the drive element having a distal end portion,
wherein the distal end portion of the drive element is connected to the proximal end portion of the transfer element.

DETAILED DESCRIPTION OF THE INVENTION

Figure 1A:
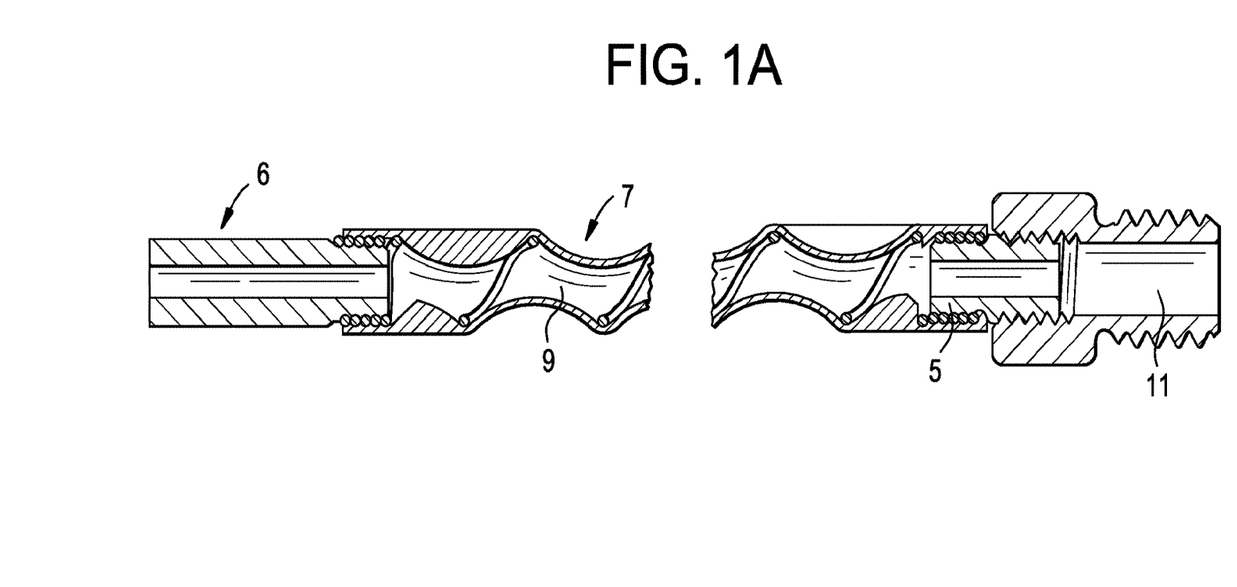
FIGS. 1A and 1B disclose a biomedical material transfer device of the present invention.
Figure 1B:
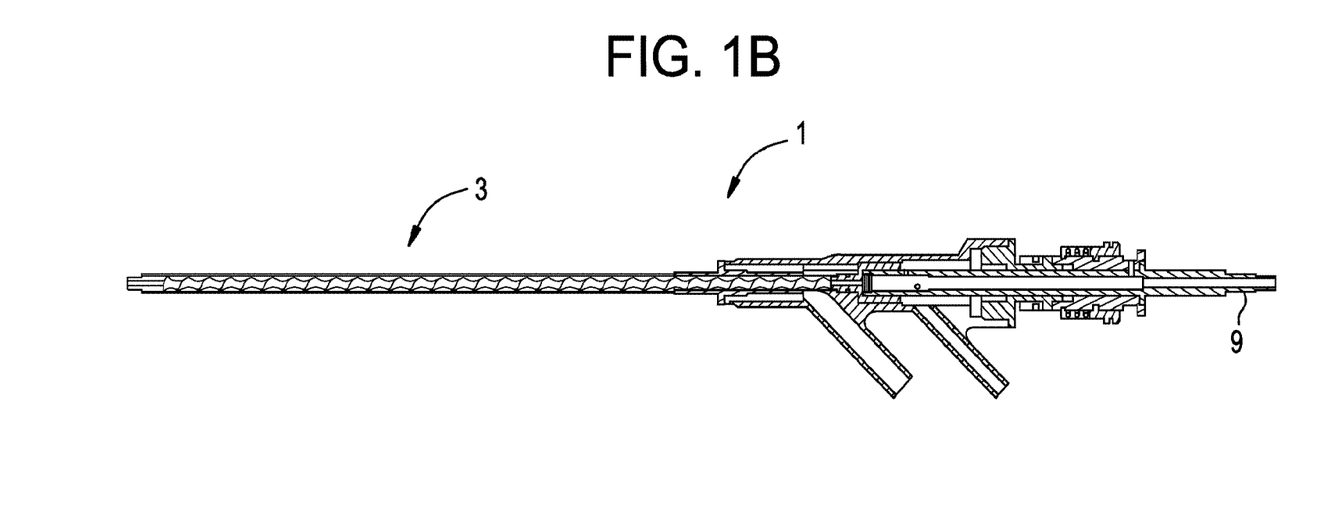

Now referring to FIGS. 1A and 1B, there is provided a biomedical material transfer device 1 comprising:
a) a transfer element 3 having a proximal end portion 5, a distal end portion 6, and an intermediate portion 7 comprising a flexible, hollow auger 7, and
b) a drive element 9 adapted to rotate the transfer element, the drive element having a distal end portion 11,
wherein the distal end portion of the drive element is connected to the proximal end portion of the transfer element.

Figure 2A:
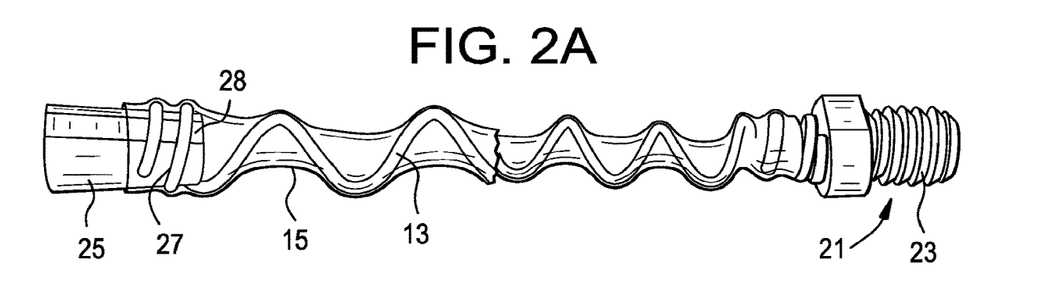
FIG. 2A discloses a second device of the present invention.
Figure 2B:
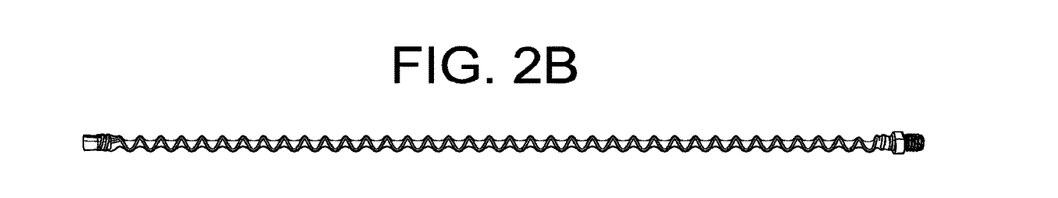
FIG. 2B discloses a second device of the present invention.
Figure 2C:
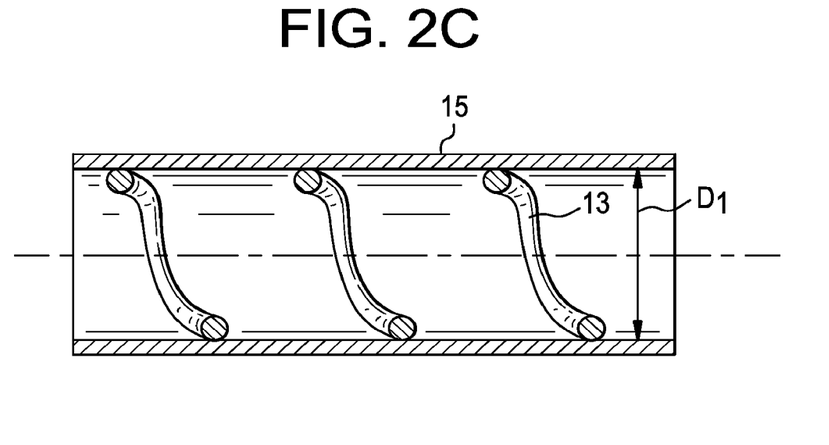
FIGS. 2C-2D disclose longitudinal cross-sections of the transfer element component of the present invention.
Figure 2D:
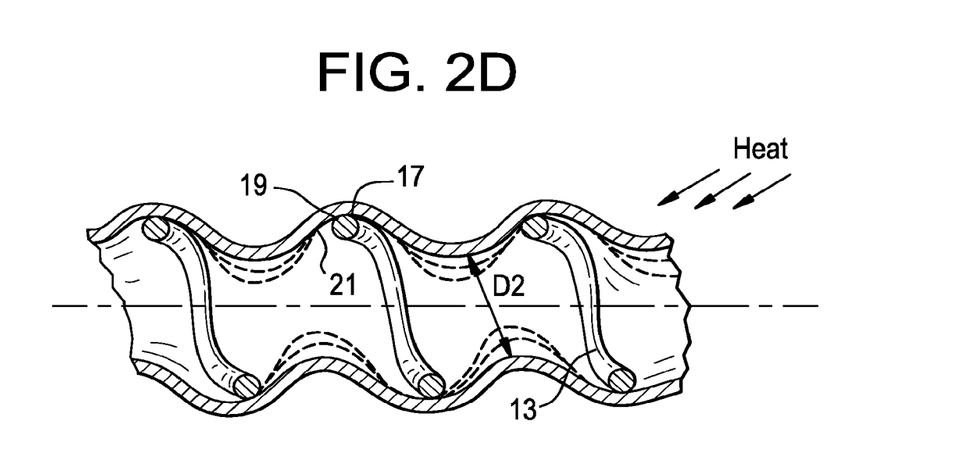

Now referring to FIG. 2AD, in one embodiment, the flexible auger is made out of a coiled mono filament such as a standard (metallic) helical spring 13 and a heat shrinkable (or dip coating) polymeric (such as PTFE) tube 15 disposed over it. The spring may be made from various materials, including metallic, polymeric-based or ceramic-based materials. Preferably, however, the spring is metallic. The helical spring has an outer diameter D1, and the shrink tube has an inner diameter substantially equivalent to the outer diameter of the helical spring, so that the outer surface 17 of the helical spring contacts the inner surface 19 of the tube. If sufficient heat is applied to the tube, the non-contact portions 21 of the tube begin to shrink to a minimum diameter D2, while the contact portions of the tube keep their original diameter D1 wherever they touch the helical spring. In this manner, the heat-shrunk tube forms "valleys and summits" and provides a thread-like appearance. The thread produced by this design is able to transport material within the auger upon rotation.

Preferably, the hollow auger comprises a tube 15 and a substantially helical element 13 housed within the tube. More preferably, the tube has an inner surface 19 and the substantially helical element extends inwardly from the inner surface.

In some embodiments, a helical coil is integrated into the tubing.

In some embodiments, the transfer element comprises a substantially helical element and a membrane wrapped around the substantially helical element. Preferably, the membrane is a heat-shrunk membrane, the substantially helical element has a first diameter D1, the tube has a first diameter D2, and, and the first diameter D1 is greater than the second diameter D2. Preferably, this tube has a thread-like topology.

Now referring to FIG. 2a, optionally, the proximal end portion of the transfer element comprises a second tube 21 having a threaded outer surface 23. This second tube of the transfer element may be integral with the substantially helical element housed within the first tube. However, this second tube of the transfer element may also be discrete from (i.e., not be integral with) the substantially helical element housed within the first tube.

In some embodiments, the second tube of the transfer element rotates with the substantially helical element housed within the first tube, while in others the substantially helical element housed within the first tube rotates independently of the second tube of the transfer element.

In some embodiments, the substantially helical element housed within the first tube has a cross-sectional thickness, and the tube has an outer diameter, and the cross-sectional thickness of the helical element is between 3% and 30% of the diameter.

Preferably, the intermediate portion of the transfer element is flexible.

Preferably, the distal end portion of the transfer element is adapted to cut intervertebral disc tissue and to fit between opposing vertebrae.

Still referring to FIG. 2a, in some embodiments, the distal end of the transfer element comprises a cutting tip 25, wherein the cutting tip has a proximal end portion 27 adapted to mate with the substantially helical element. Preferably, the distal end of the transfer element comprises a distal end opening (not shown).

Typically, the drive element 9 comprises either a drive handle or a motor.

In some embodiments, the device further comprises a tubular shaft surrounding the transfer element and connected to the housing that surrounds the drive element, this housing having a relative rotational or translational movement to the drive element. The tubular shaft is optionally transparent.

Figure 3A:
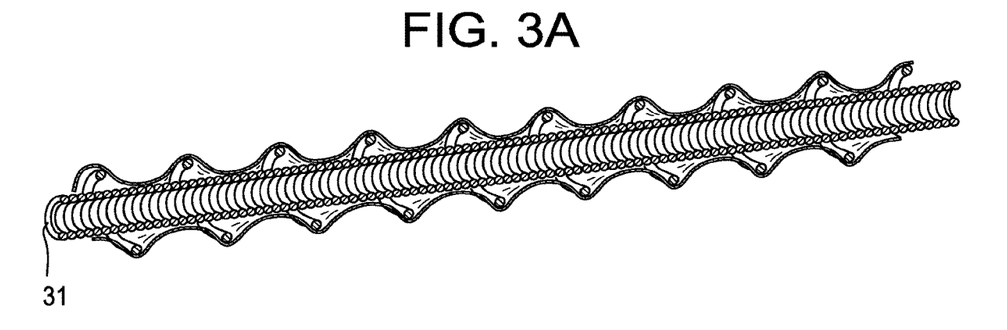
FIGS. 3A-B disclose the device of the present invention further comprising a flexible inner shaft disposed within the hollow auger.
Figure 3B:
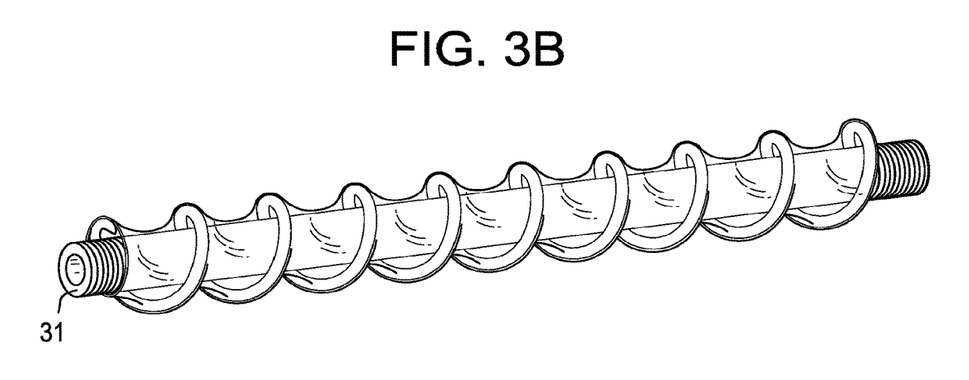

Now referring to FIGS. 3A and 3B, in some embodiments, the device further comprises a flexible inner shaft 31 disposed within the hollow auger. Preferably, the flexible inner shaft is hollow. Preferably, the flexible inner shaft comprises a narrow-wound spring.

In some embodiments, the device further comprises an outer cannula, wherein the hollow auger is disposed within the outer cannula. In some embodiments, the outer cannula comprises a wall and an inner bore, wherein the wall has at least one lumen therein.

In some embodiments, the device further comprises a wire running longitudinally in the lumen. Preferably, the outer cannula comprises a wall and an inner bore, wherein the wall has at least one stationary wire running longitudinally therein.

In some embodiments, the hollow auger has one or more steering mechanisms attached thereto. These steering mechanisms may include at least one pulling mechanism, or at least one pushing mechanism, or a combination thereof.

In some embodiments, the proximal end portion of the transfer element is more rigid than the hollow auger.

In some embodiments, the proximal end portion of the transfer element comprises an inlet adapted to provide fluid transfer (for purposes such as irrigation, heating or cooling) to a space between the flexible auger and the flexible inner shaft.

In some embodiments, the proximal end portion of the transfer element comprises an inlet adapted to provide fluid transfer (for purposes such as irrigation, heating or cooling) to a space between the flexible auger and the outer cannula.

In some embodiments, the hollow auger has a length having a variable bending stiffness.

The stated pitch of the auger communicates the number of turns of the helix over a given distance. The pitch determines the ratio between speed and force during tissue removal. A steeply-pitched auger (i.e., a few turns per millimeter) is able to remove material more quickly than a shallow-pitched auger. However, a shallow pitched auger enables better force transmission than the steeper pitch. Hence, there is a tradeoff in pitch with respect to the desirable speed and force qualities. In preferred embodiments, the pitch of the flexible auger is between 3.5 and 7.0 mm.

It is believed that the variable pitch embodiments of the present invention may be advantageous in applications involving material delivery.

Figure 4A:
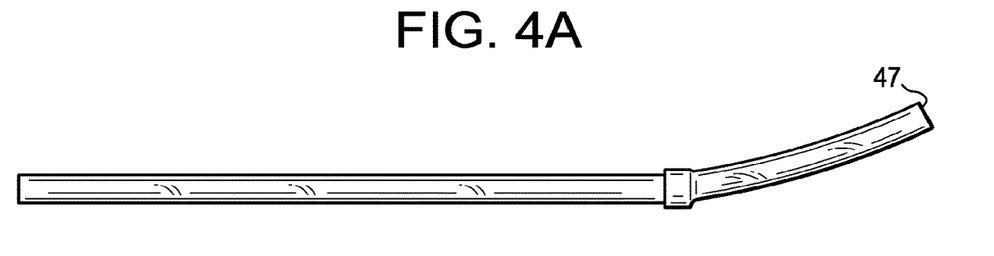
FIGS. 4A and 4B disclose various geometries of the opening at the distal end portion of the transfer element.
Figure 4B:
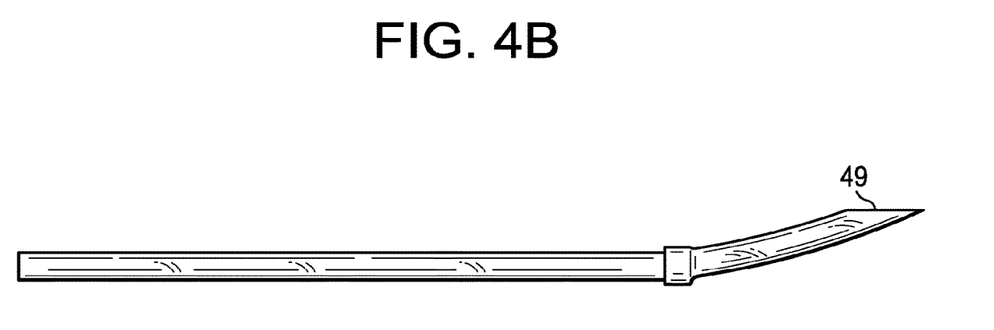

The geometry of the opening at the distal end portion of the transfer element determines how tissue enters the auger. As shown in FIG. 4A, a straight tip 47 (i.e. an edge perpendicular to the longitudinal axis) only allows material to enter from directly in front of the auger, whereas an angled tip 49 (as shown in FIG. 4B) allows material to enter from one side of the auger. One angled tip embodiment comprises a distal opening cut at 30° relative to the straight tip. Preferably, the outer diameter of the opening of the distal end portion of the transfer element is less than 10 mm. In some embodiments, the distal end portion of the transfer element is a tube having a length of about 60 mm and an articulation radius of 15-21 mm (as measured at the inside of the bend).

In some embodiments, the overall length of the material transfer element is between about 10 mm and 1000 mm, and preferably approximately 220 mm.

In some embodiments, the distal end portion of the transfer element has an outer diameter of no more than 30 mm.

In some embodiments, the distal end portion of the transfer element comprises a cutting tip adapted to cut intervertebral disc tissue, so that the overall device is a tissue removal device. Typically, a robust, inexpensive coupling method is carried out to connect the distal cutting tip to the intermediate auger. This coupling method should provide strength to the overall device and allow (e.g., not impede) tissue transport. In one coupling embodiment, the proximal end portion 27 of the cutting tip 25 is provided with a helical channel 28 to mate with the distal end portion of the helix of the hollow auger. In other embodiments, the distal end portion of the helix may be spot welded to the proximal end portion of the cutting tip.

In one embodiment, the tissue removal device comprises a flexible central shaft and a helically-shaped shrink tube (i.e., without a helical coil). The first step in the manufacture of this embodiment involves making the transfer device described above, inserting a flexible shaft down its center bore, and then removing the helical coil by screwing it out of the assembly, thereby leaving behind the helically-shaped shrinktube disposed over the flexible central shaft.

Therefore, in accordance with the present invention, there is provided a material transfer device comprising:
  a) a transfer element having a proximal end portion, a distal end portion, and an intermediate portion consisting of a flexible membrane having a threadform shape and a flexible central shaft housed longitudinally within the membrane,
  b) a drive element adapted to rotate the transfer element, the drive element having a distal end portion,
  wherein the distal end portion of the drive element is connected to the proximal end portion of the transfer element.

In one embodiment, the material transfer device consists of a flexible central shaft surrounded by a helical coil (i.e., without the shrink tube). If the particles-to-be-transported have an adequate size and sufficient viscosity, a flexible central shaft surrounded by a "floating" helical coil can be sufficient to transport that material. This coil can be moved axially relative to the central shaft to effect particle transport, or rotated relative to the central shaft, or both. Axial movement of the coil can include both advancement and retraction.

Therefore, in accordance with the present invention, there is provided a material transfer device comprising:
  a) a transfer element having a proximal end portion, a distal end portion, and an intermediate portion consisting of a flexible helix and a flexible shaft housed within the helix,
  b) a drive element adapted to rotate the transfer element, the drive element having a distal end portion,
  wherein the distal end portion of the drive element is connected to the proximal end portion of the transfer element.

In one embodiment, the transfer element comprises a flexible central shaft surrounded by a flexible helical coil, which is surrounded by a flexible heat-shrink tube.

In one embodiment, this flexible central shaft could be formed from a narrow-wound helical spring.

Figure 5A:
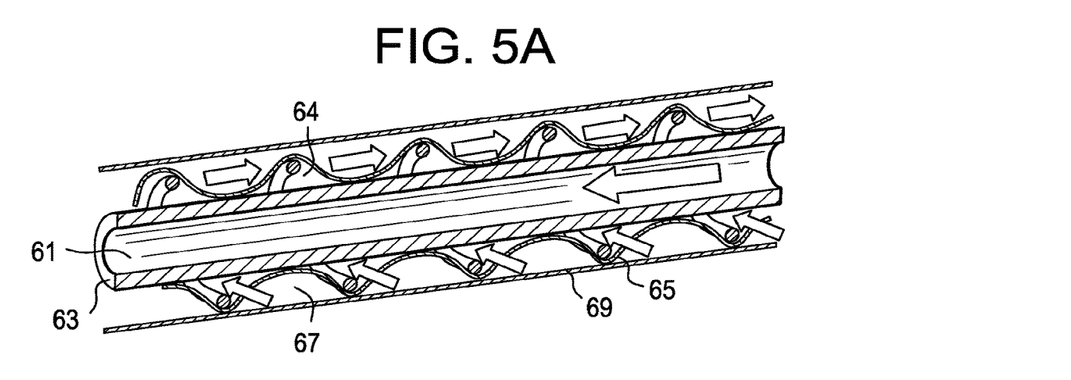
FIGS. 5A-C disclose the device of the present invention further comprising a flexible inner tube disposed within the hollow auger.
Figure 5B:
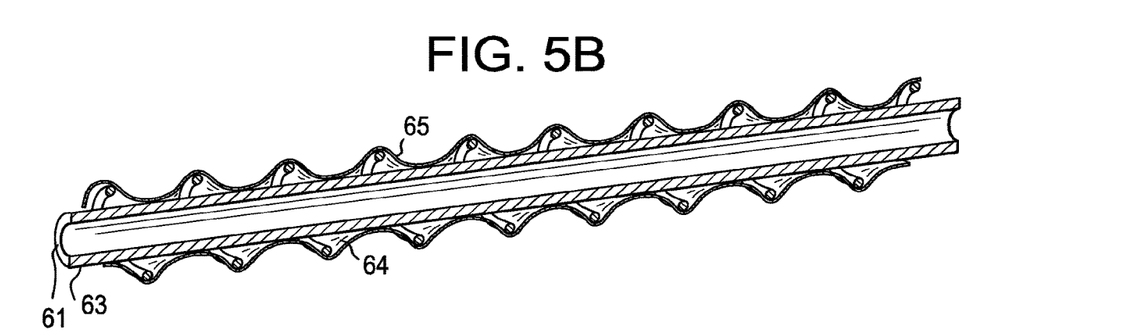
Figure 5C:
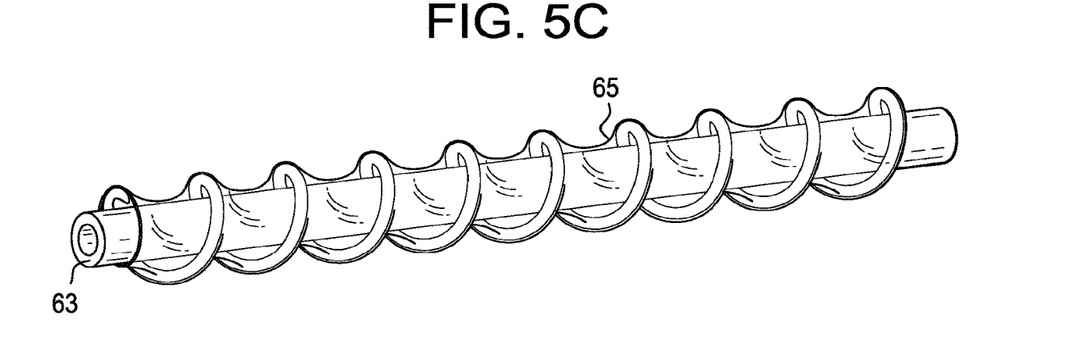

In some embodiments, and now referring to FIGS. 5A-C the device comprises a cannulated torque-transmitting inner flexible shaft disposed in a flexible hollow auger, which in turn is disposed in an outer cannula. In such an embodiment, there may be three working lumens:
  a) a cylindrical lumen 61 within the cannulated torque transmitting shaft 63 (this lumen can be used for placement of a flexible guide wire);
  b) a first helical lumen 64 between the auger membrane wall 65 and the torque transmitting shaft (this lumen can be used for irrigation); and
  c) a second helical lumen 67 between the auger membrane and the outer cannula 69 (this lumen can be used for material transport).

Figure 6:
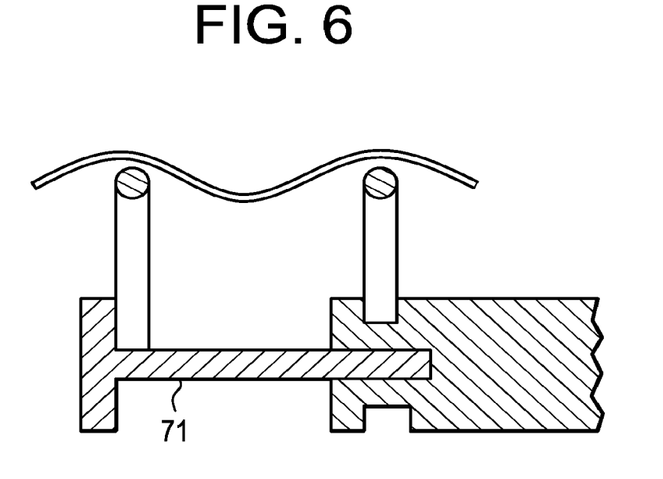
FIG. 6 discloses a pulling mechanism.

In some embodiments, and now referring to FIG. 6, the device has one or more pulling mechanisms 71 attached to the hollow auger that can simultaneously manipulate both the helical coil pitch and diameter.

Figure 7:
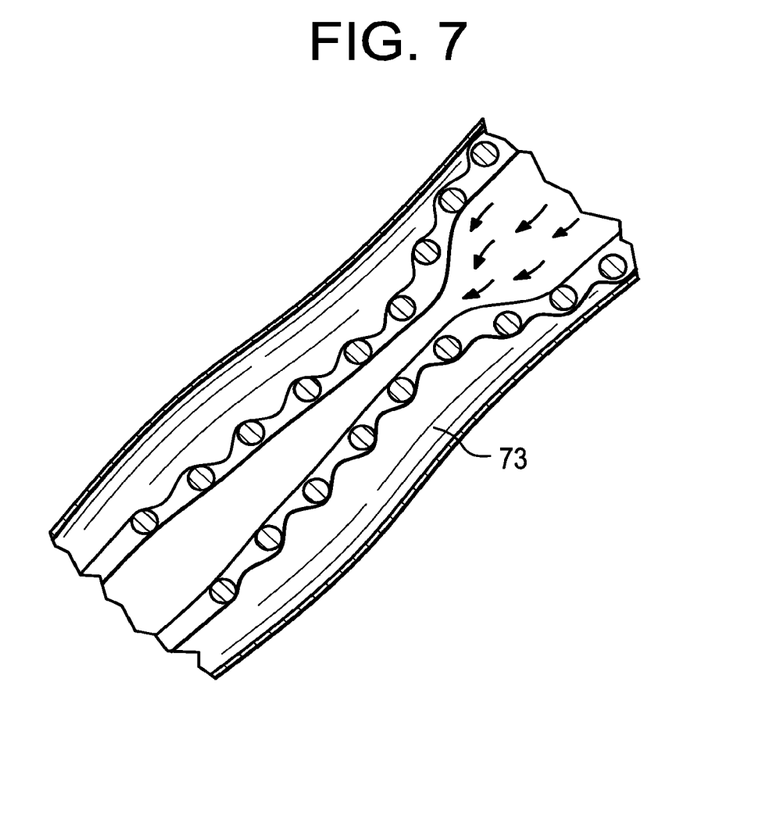
FIG. 7 discloses a necked flexible auger of the present invention.

Within narrow curves, and now referring to FIG. 7, the outer diameter of the flexible auger could be made permanently slightly smaller in order to prevent contact/friction with the outer cannula. This embodiment provides a clearance between the helix and the cannula. The manufacture of this neck 73 can also be achieved in a very cost effective manner with helical springs.

In another embodiment, the bending stiffness along the flexible auger could be varied by producing the heat-shrink tube via an intermittent extrusion process, as described in U.S. Pat. No. 4,888,146, the specification of which is incorporated by reference in its entirety. This process can provide a soft tip or a combination of flexibility and stiffness for insertion. In many cases, such extrusions are used to replace manually assembled composite shaft constructions (i.e. hand layups)."

In some embodiments, the proximal portion of the transfer element is designed to be rigid in order to stabilize turning movement and bearing in case of torque transmission. In some embodiments thereof, the end of the shrink tube itself might be the bearing surface.

Figure 8:
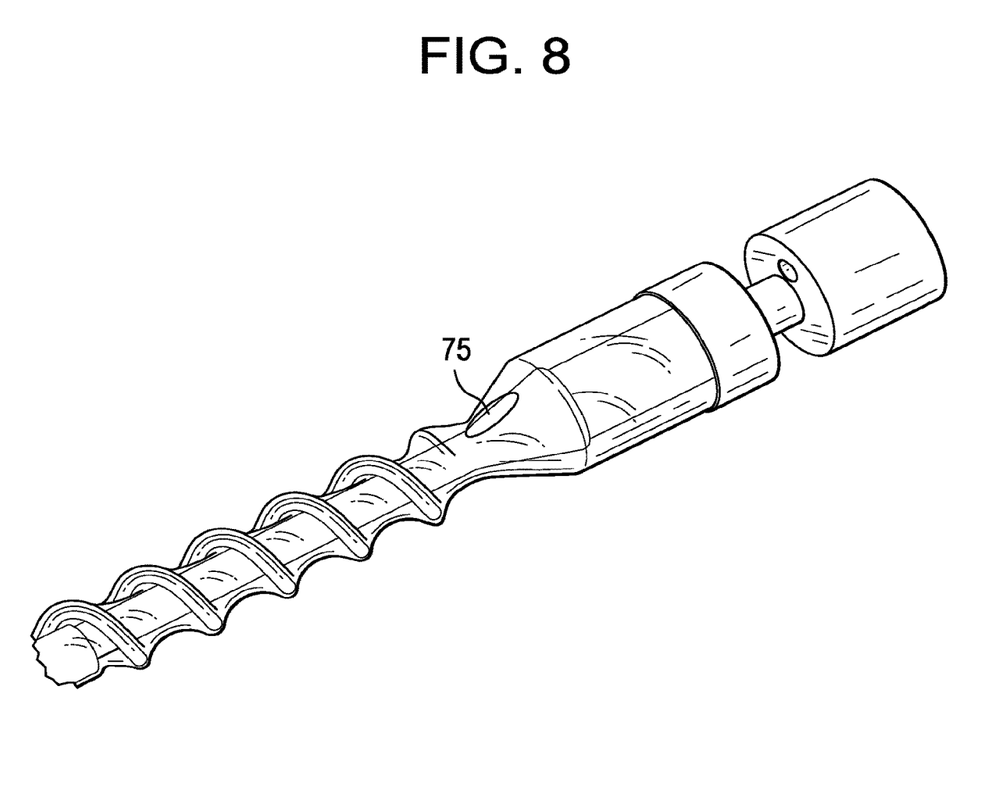
FIG. 8 disclose the device of the present invention having an inlet for fluid passage.

In some embodiments, and now referring to FIG. 8, the proximal portion of the transfer element comprises a sealable inlet 75 that provides irrigation into the space between the hollow auger and the inner shaft. Alternatively, the proximal portion of the transfer element comprises a sealable inlet that provides irrigation into the space between the hollow auger and the outer cannula. The inlet may also allow the provision of a) fluids that provide heating or cooling, or b) material delivery as well. The inlet is one possible design feature that allows providing cooling fluid/irrigation/material transport from outside to the lumen between the flexible inner shaft and shrink tube of the embodiments described in FIGS. 5A-C.

Figure 9:
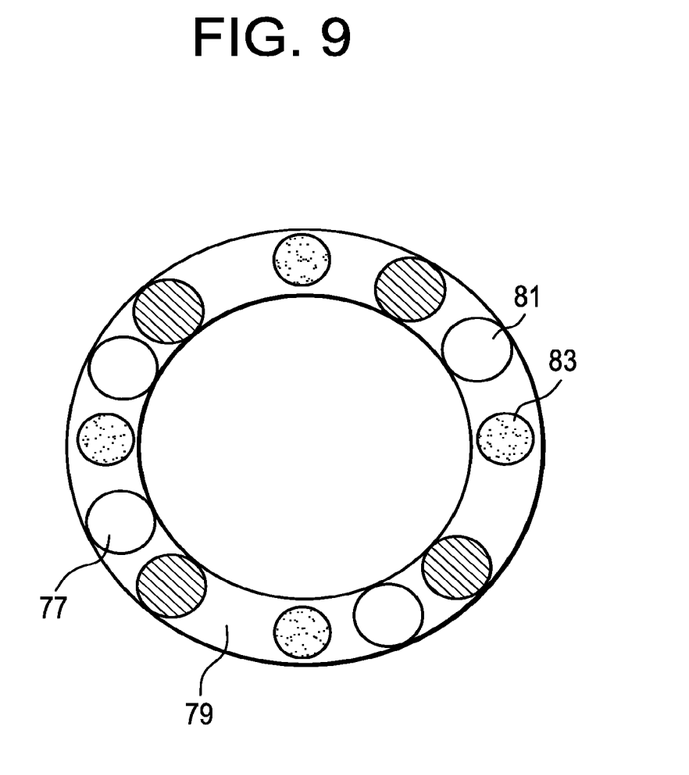
FIG. 9 discloses a cross-section of the outer cannula that surrounds the flexible auger, wherein a plurality of lumens are disposed in the cannula wall.

In some embodiments, and now referring to FIG. 9, there is at least one lumen 77 disposed in the wall 79 of the outer cannula that surrounds the flexible auger. This lumen can be used to perform various functions. For example, a surgeon could perform device steering by pulling or pushing strings that run through such a lumen in the outer cannula wall. Another lumen in the outer cannula wall could provide irrigation. Yet another lumen 81 in the outer cannula wall could allow visualization by providing imaging means (such as optical fibres) that run through the lumen. Therefore, in some embodiments, the cannula that surrounds the flexible auger comprises a wall and an inner bore, wherein the wall has at least one longitudinal lumen therein. In some embodiments, the outer cannula can have two or more lumens of similar size and shape, or of varying sizes and shapes. One common two lumen configuration, sometimes referred to as a double-D, may be used for a peripherally-inserted central cannula (or PICC lines). PICC lines may also have three lumens with a cross-sectional view that represents a 'peace sign.' Two- and three-lumen configurations in which the lumens are dissimilar in size and shape are frequently used for percutaneuous transluminal coronary angioplasty (PTCA) catheters. More simple cannulae, such as those used for drainage, may require only one lumen. Other applications, such as drug atomizing devices, may require tubing with more than a dozen lumens.

In some embodiments, reinforced wire technology could be adopted to achieve steering capabilities of the outer cannula that surrounds the flexible auger. These wires 83 are housed in the above-described lumen and should be able to be moved axially in order to provide a push/pull steering capability.

In other embodiments, the cannula comprises a wall and an inner bore, wherein the wall has at least one stationary wire running longitudinally therein. Longitudinal wires or fibers incorporated into an extrusion cross-section provide specific benefits, such as structural support or electrical data transmission. Wires can also provide excellent stretch resistance but limits flexibility depending on the number and location of reinforcing members. It is also possible to combine braided or spiral reinforcing with linear reinforcing elements to produce a hybrid design. Reinforcement material, tensile strength, size, and placement of the elements are critical aspects with linear reinforcing. High-tensile stainless steel round wire is commonly used for wire reinforcing. In thin wall sections, flat wire provides an excellent alternative. Other materials, such as aramid fiber or polymer monofilaments, can also be used for specialty linear reinforcement applications.

In some embodiments, the outer cannula could comprise an elastomer bulk with an internal metal wire pattern for reinforcement. The arrangement of the wire pattern can determine the outer cannula's ability to flex in certain directions, while being stiffer in other directions.

In some embodiments, the helical element in the flexible auger is a standard helical spring. Typically, this spring can be made out of biocompatible metals, such as titanium alloy, stainless steel and cobalt chrome. In some embodiments, the tube component of the flexible auger is a tube made out of heat shrink material. Typically, the heat shrink material is a polymeric, such as a PTFE.

Also in accordance with the present invention, there is provided a method comprising the steps of:
a) passing a helical spring into a tube comprising a heat-shrink material,
b) heating the tube to effect shrinking of the tube onto the helical spring to form an auger,
c) inserting the auger into an intervertebral disc,
d) rotating the auger to effect removal of intervertebral disc material.

In addition to the above-described heat shrink method of making the auger of the present invention, there is further contemplated additional embodiments of creating a flexible auger that entail low manufacturing costs.

In a first embodiment, the method comprises physically expanding a tube over a helical spring and then letting the tube contract. In this embodiment, the tube member in its initial state has an inner diameter ID that is smaller than the outer diameter OD of the spring. The tube can then be physically expanded in diameter by known methods (e.g., with high-pressure air, or with heat) until it reaches a dimension where its ID is larger than the OD of the spring. In this expanded condition, the tube is passed over the spring. When the force/energy upon the tube is removed, the tube in this assembly reverts to its original dimensions, except in the locations where it touches the helical spring member. The resulting product is an auger-like assembly with peaks and valleys.

Therefore, in accordance with the present invention, there is provided a method comprising the steps of:
a) applying a physical force upon a tube to expand the tube,
b) passing a helical spring into the expanded tube,
c) releasing the physical force upon the tube to effect shrinking of the tube onto the helical spring to form an auger, d) inserting the auger into an intervertebral disc,
e) rotating the auger to effect removal of intervertebral disc material.

In a second embodiment, the method comprises radially compressing the helical spring and then applying heat to the spring to allow its stressed areas to expand to a larger diameter. In this embodiment, the helical spring's outer diameter is reduced from its resting state (e.g., by winding the helical spring very tightly, or by pulling the helical member and thereby producing an elongated spring having a smaller outer diameter). In this reduced-diameter configuration, the radially compressed spring can be inserted into the tube member. Upon release of the mechanical force causing diameter reduction, the helical spring reverts to its original dimensions. Because the tube member possesses some flexibility, the elastic nature of the tube allows it to be deformed by the pressure of the expanding helical member upon the tube ID. Another auger-like assembly with valleys and summits is thereby produced.

Therefore, in accordance with the present invention, there is provided a method comprising the steps of:
a) applying a physical force upon a helical spring to radially compress the spring,
b) passing the compressed helical spring into a tube having an inner diameter,
c) heating the compressed spring to effect radial expansion of the helical spring so as to contact the inner diameter of the tube and form an auger,
d) inserting the auger into an intervertebral disc,
e) rotating the auger to effect removal of intervertebral disc material.

In a third embodiment, the method comprises simultaneously applying heat and vacuum to an ordinary polymeric tube to obtain the same effect as a heat shrink. In this embodiment, the tube member is made of a material that is not heat-shrinkable, but rather is plastically deformable under heat and so over time arrives at an elastomeric state. In this embodiment, the tube member has an inner diameter ID in its initial state that is larger than the outer diameter OD of the helical spring, so that the helical member can be inserted into the tube member. Once the spring is inside the tube, a low pressure region/vacuum is created inside of the tube member, and the tube member is heated at the same time. These conditions create deformation in the wall of the tube member caused by the vacuum pulling towards the center of the tube. This reduces the diameter of the tube member, except for the locations where the helical member contacts the inside of the tube and so prevents deformation of the tube member in these areas. This results in another auger-like assembly with valleys and summits.

Therefore, in accordance with the present invention, there is provided a method comprising the steps of:
a) passing a helical spring into a tube having a bore and comprising a polymeric material,
b) simultaneously heating the tube and applying a vacuum to the bore of the tube to effect shrinking of the tube onto the helical spring to form an auger,
c) inserting the auger into an intervertebral disc,
d) rotating the auger to effect removal of intervertebral disc material.

We claim:

1. A surgical method, comprising:
guiding a distal end portion of a material transfer device to a surgical site;
irrigating the surgical site by passing fluid distally from an inlet formed in a proximal end portion of the device through a first helical lumen formed between a hollow auger and a flexible inner shaft of the transfer device; and
transporting material from the distal end portion of the transfer device toward the proximal end portion through a second helical lumen formed between an outer cannula and the hollow auger.

2. The method of claim 1, wherein the surgical site is an intervertebral disc.

3. The method of claim 1, wherein transporting material is effected by rotating the hollow auger and the flexible inner shaft of the transfer device.

4. The method of claim 3, wherein rotating the hollow auger and the flexible inner shaft of the transport device is done using a drive element coupled to a proximal end portion of the flexible inner shaft.

5. The method of claim 1, wherein the outer cannula, the hollow auger, and the flexible inner shaft are guided simultaneously to the surgical site.

6. The method of claim 1, wherein guiding the distal end of the material transfer device includes guiding the outer cannula to the surgical site prior to guiding the hollow auger and the flexible inner shaft to the surgical site.

7. The method of claim 1, wherein guiding the distal end of the material transfer device includes passing a guidewire through an inner lumen of the flexible inner shaft of the transport device.

8. The method of claim 1, further comprising steering the material transfer device by any of axially pushing and pulling a wire passing through a lumen formed in a wall of the outer cannula.

9. The method of claim 1, further comprising simultaneously adjusting a helical coil pitch and diameter of the hollow auger by axially pulling a wire attached thereto.

10. The method of claim 1, further comprising irrigating the surgical site by passing fluid distally through a lumen formed in a wall of the outer cannula.

11. The method of claim 1, further comprising visualizing the surgical site using a visual apparatus disposed in a lumen formed in a wall of the outer cannula.

* * * * *